US011187700B1

(12) United States Patent
Kemmann

(10) Patent No.: US 11,187,700 B1
(45) Date of Patent: Nov. 30, 2021

(54) CLOSED SYSTEM FOR ENLARGING VIRAL AND BACTERIAL PARTICLES FOR IDENTIFICATION BY DIFFRACTION SCANNING

(71) Applicant: Eckhard Kemmann, Bridgewater, NJ (US)

(72) Inventor: Eckhard Kemmann, Bridgewater, NJ (US)

( * ) Notice: Subject to any disclaimer, the term of this patent is extended or adjusted under 35 U.S.C. 154(b) by 0 days.

(21) Appl. No.: 17/161,462

(22) Filed: Jan. 28, 2021

(51) Int. Cl.
*G01N 33/536* (2006.01)
*G01N 33/543* (2006.01)
*G01N 33/569* (2006.01)

(52) U.S. Cl.
CPC . *G01N 33/54373* (2013.01); *G01N 33/56911* (2013.01); *G01N 33/56983* (2013.01)

(58) Field of Classification Search
CPC ....... G01N 33/56911; G01N 33/56983; G01N 33/54373; G01N 21/4788; G01N 23/2055; G01N 2223/056; G01N 2223/0566
USPC .................. 435/287.2, 5, 7.32, 288.1, 288.7; 422/82.05; 436/164, 805
See application file for complete search history.

(56) References Cited

U.S. PATENT DOCUMENTS 6,171,486 B1 * 1/2001 Green .................... B01D 15/22 210/198.2
6,660,498 B1 * 12/2003 Hui ......................... A61P 33/06 435/69.1
2002/0142414 A1 * 10/2002 Rink .................... C07K 14/815 435/183
2003/0008321 A1 * 1/2003 Fukui ..................... C07K 16/18 435/7.1
2006/0111668 A1 * 5/2006 Baik ..................... A61M 5/322 604/110
2016/0280744 A1 * 9/2016 Honda ................... C07K 14/31
2019/0169278 A1 * 6/2019 Dixit .................. A61K 47/6803

OTHER PUBLICATIONS

Wyatt Technologies DAWN detector ((Wyatt Technologies, DAWN light scattering detector, https://www.wyatt.com/products/instruments/multi-angle-light-scattering-detectors-sec-mals.html) (Year: 2021).*

* cited by examiner

*Primary Examiner* — Christopher L Chin

(57) ABSTRACT

A closed system is provided for enlarging viral and bacterial particles for identification by diffraction scanning. The closed system includes a transparent tube, a deformable dispenser, a quantity of first antibodies, a quantity of second antibodies, and a diffraction scanning device. The transparent tube contains the quantity of first antibodies, the quantity of second antibodies, and receives the exhaled air from an individual. The deformable dispenser drives the quantity of second antibodies to mix with a complex formed by target matter in the exhaled air and the quantity of first antibodies. The quantity of first antibodies interacts with the target matter. The quantity of second antibodies interacts with the complex formed by the target matter and the quantity of first antibodies. The diffraction scanning device measures the number and size of particles within the transparent tube.

16 Claims, 6 Drawing Sheets

CLOSED SYSTEM FOR ENLARGING VIRAL AND BACTERIAL PARTICLES FOR IDENTIFICATION BY DIFFRACTION SCANNING

FIELD OF THE INVENTION

The present invention relates generally to applications for virus and bacterial infections. More specifically, the present invention is a closed system for enlarging viral and bacterial particles for identification by diffraction scanning. The present invention uses antibodies to enlarge the size of the viral or other particular matter under investigation to such a degree that it can be identified by a diffraction scanning device.

BACKGROUND OF THE INVENTION

There are many viral and bacterial diseases that are sometimes misdiagnosed due to a lack of efficient and easy viral and bacterial infection tests. A misdiagnosis can lead to a prolonged recovery because an individual may not be taking the necessary steps in order to treat the actual virus or bacterial infection. Additionally, there are tests available which are accurate, but the results are not immediately provided to the individual. Moreover, some tests can be uncomfortable for individuals. For example, some tests involve using swabs to retrieve matter from either the back of the throat or from the nasal passages of the individual. There is a need for an accurate, rapid, and comfortable test system which allows an individual to quickly take the necessary steps for recovery.

It is therefore an objective of the present invention to provide a closed system for enlarging viral and bacterial particles for identification by diffraction scanning. The present invention includes a transparent tube and the ends of the transparent tube are closed off by a deformable dispenser and a cap. Thus, the present invention is a closed system. The present invention uses two sets of monoclonal antibodies and a diffraction scanning device in order to identify the presence of viral or other particular matter. If necessary, more layers of antibodies could be applied to enlarge the formed matter-antibody complex whereby each new antibody reacts with the preceding complex of target matter plus already applied antibodies.

The diffraction scanning device accurately measures the number and size of the particles within the transparent tube. The number and size of the particles are then compared to established normal values in order to determine the presence of viral or other particular matter in the exhaled air. The present invention is a blow test which is more comfortable for individuals than other types of tests that involve using a swab to retrieve matter from the back of the throat or from nasal passages. Moreover, the present invention immediately provides results to the individual allowing the individual to quickly take the necessary steps for recovery.

DETAIL DESCRIPTIONS OF THE INVENTION

Figure 1:
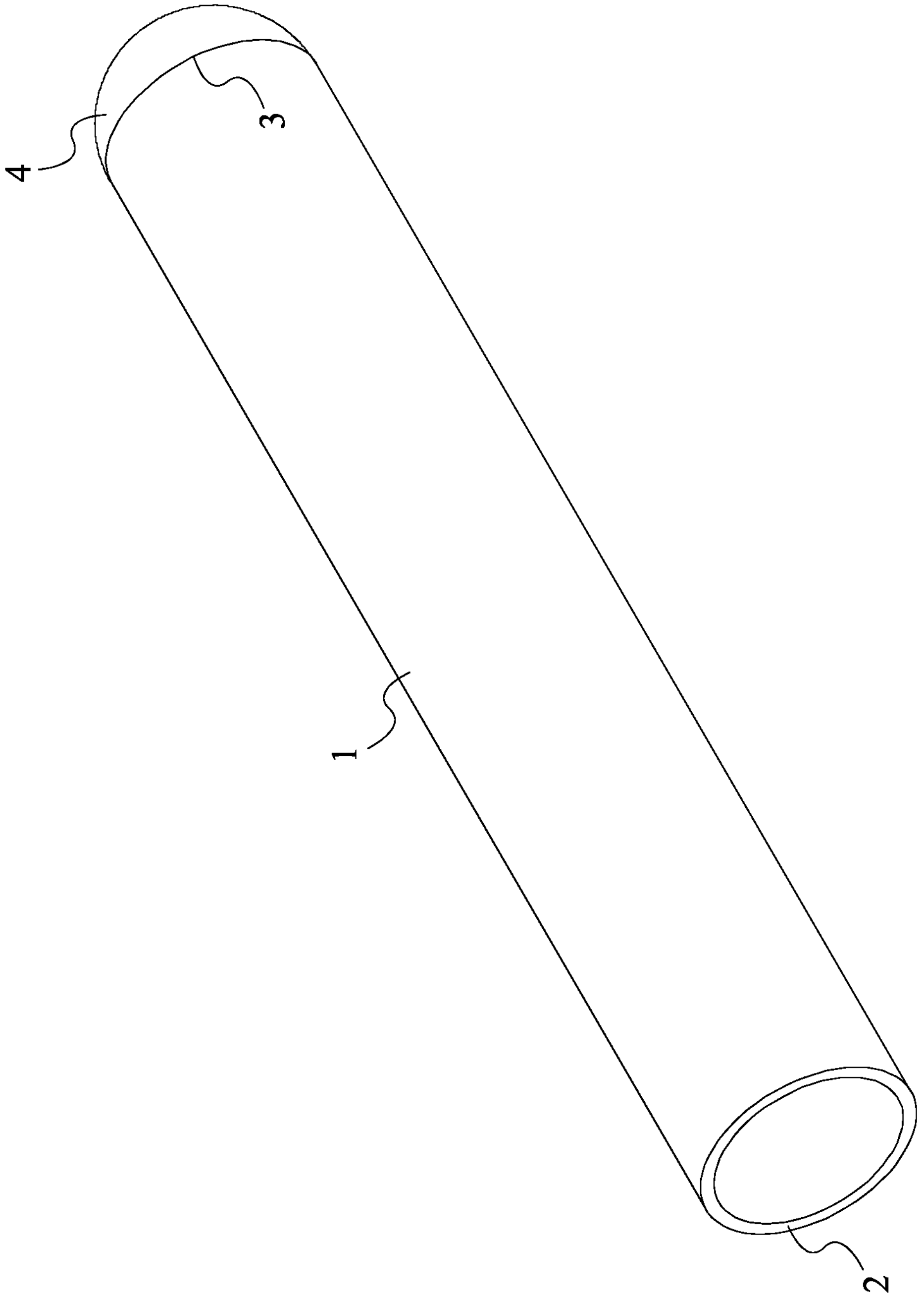
FIG. 1 is a perspective view of the present invention in an open state.
Figure 2:
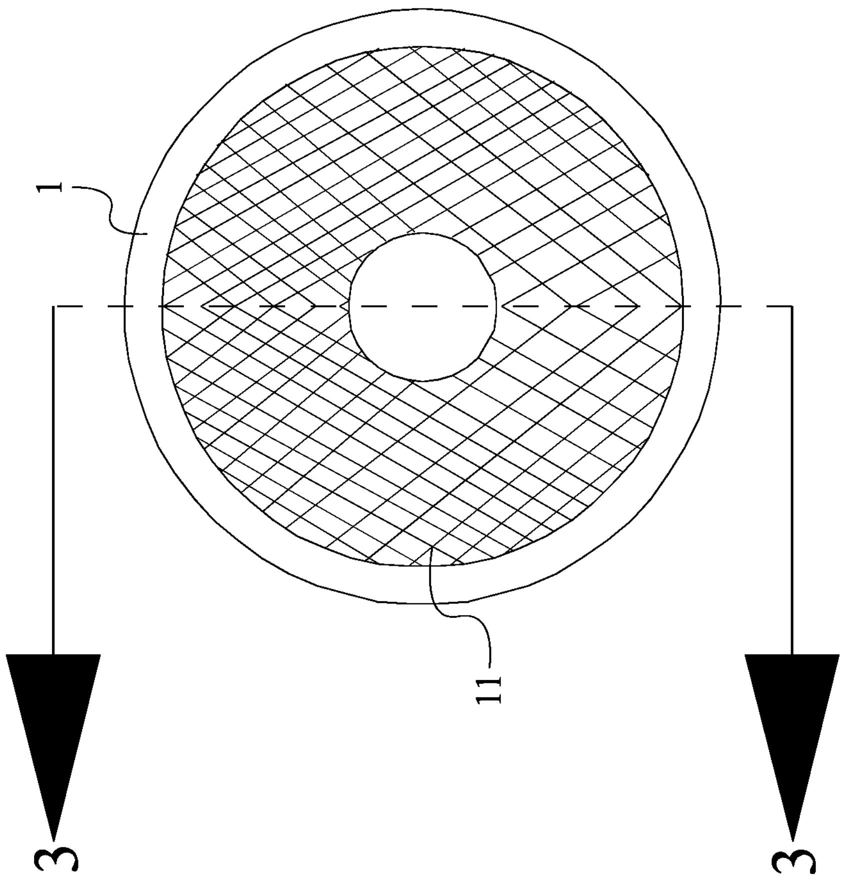
FIG. 2 is a front view of the present invention in the open state.

All illustrations of the drawings are for the purpose of describing selected versions of the present invention and are not intended to limit the scope of the present invention.

In reference to FIGS. 1 through 6, the present invention is a closed system for enlarging viral and bacterial particles for identification by diffraction scanning. The preferred embodiment of the present invention comprises a transparent tube 1, a deformable dispenser 4, a quantity of first antibodies 7, a quantity of second antibodies 8, and a diffraction scanning device 9. The transparent tube 1 contains the quantity of first antibodies 7, the quantity of second antibodies 8, and receives the exhaled air from an individual. The exhaled air from the individual can be coughed air in order to produce more viral or other particular matter to be transmitted into the transparent tube 1. The viral or other particular matter can be referred as target matter. The transparent tube 1 allows the diffraction scanning device 9 to efficiently measure the size and number of particles within the transparent tube 1 after the exhaled air interacts with the quantity of first antibodies 7 and the quantity of second antibodies 8. The deformable dispenser 4 allows an individual to manually drive the quantity of second antibodies 8 in order to mix with a complex formed by target matter in the exhaled air and the quantity of first antibodies 7. The quantity of first antibodies 7 is initially directed against the exhaled air in order to attach to the target matter which may be present in the exhaled air. The quantity of second antibodies 8 is subsequently directed against the complex formed by the target matter in the exhaled air and the quantity of first antibodies 7. This creates a set of bound antibodies of a specific size that can be identified. The diffraction scanning device 9 measures the number and size of particles within the transparent tube 1. Thus, the presence of the target matter bound to the quantity of first antibodies 7 and further bound to the quantity of second antibodies 8 form particles of a defined size that will be noted by a diffraction measurement, while in the absence of the antibody interaction, this specific particle size accumulation will not be noted by a diffraction measurement. The expected particle size in a positive test is a function of the size of the target matter plus the size of the quantity of first antibodies 7 plus the size of the quantity of second antibodies 8, and the amount of this complex determined by diffraction correlates to the amount of target matter. In a negative test, only the quantity of first antibodies 7 and the quantity of second antibodies 8 will be noted by diffraction at their individual size.

Figure 3:
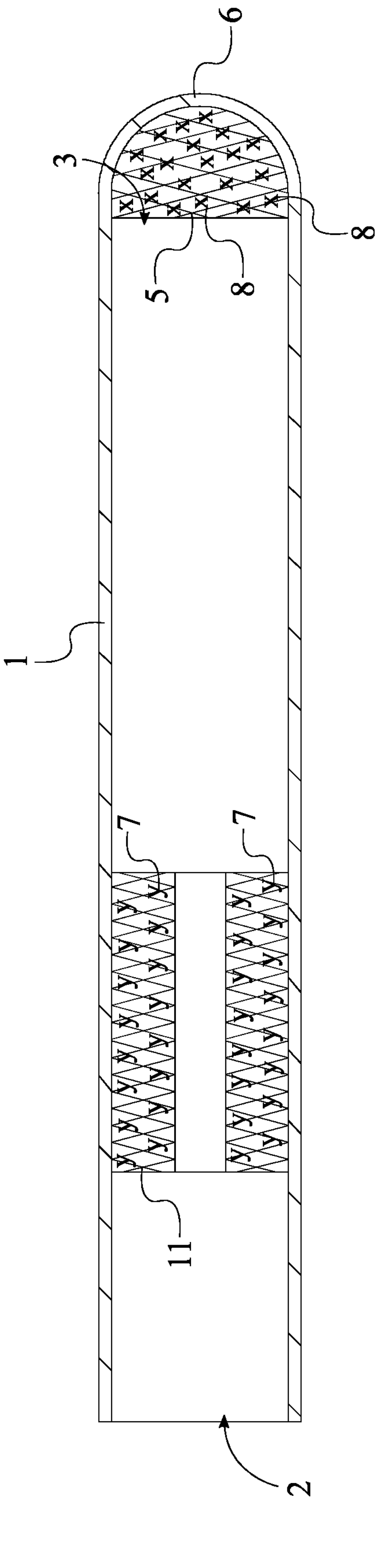
FIG. 3 is a cross-sectional view taken along line 3-3 in FIG. 2.
Figure 6:
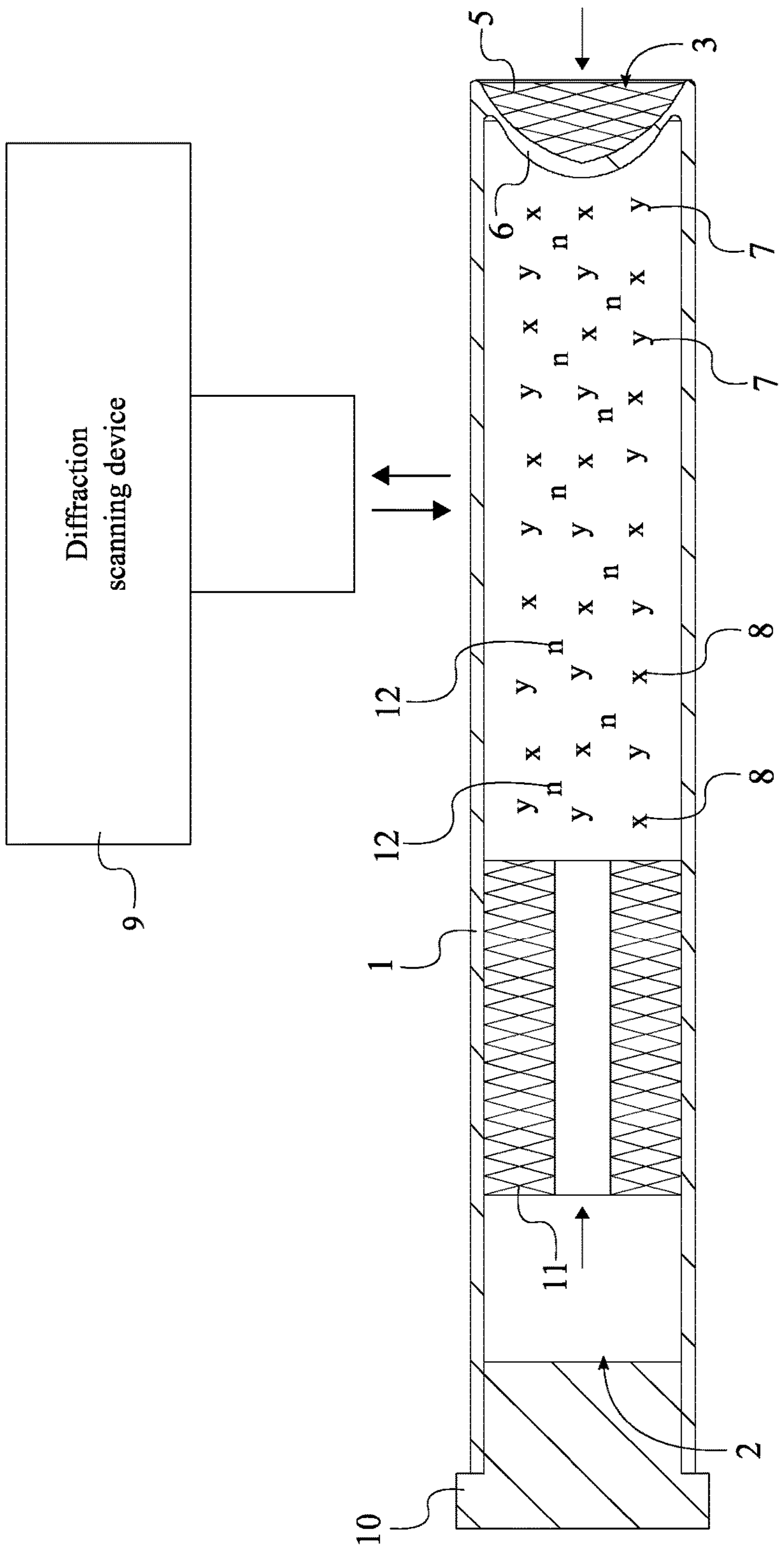
FIG. 6 is a cross-sectional view taken along line 6-6 in FIG. 5.

The general configuration of the aforementioned components allows the present invention to identify the presence of viral or other particular matter in exhaled air. With reference to FIGS. 1 and 3, the transparent tube 1 comprises a first open end 2 and a second open end 3. The deformable dispenser 4 is hermetically connected to the second open end 3. Thus, the second open end 3 of the transparent tube 1 is closed off. Further, this arrangement provides an airtight connection between the deformable dispenser 4 and the transparent tube 1. The quantity of first antibodies 7 is suspended within the transparent tube 1, adjacent to the first open end 2. The quantity of first antibodies 7 may be suspended within the transparent tube 1 through various methods. Further, this arrangement allows the quantity of first antibodies 7 to first contact the exhaled air when released into the transparent tube 1. Similarly, the quantity of second antibodies 8 is suspended within the deformable dispenser 4. The quantity of second antibodies 8 may be suspended within the deformable dispenser 4 through various methods. This arrangement ensures that the quantity of second antibodies 8 does not prematurely mix with the exhaled air or the quantity of first antibodies 7. With reference to FIG. 6, the diffraction scanning device 9 is positioned offset from the transparent tube 1 and is in optical communication with the transparent tube 1. Thus, the diffraction scanning device 9 can easily and efficiently scan the transparent tube 1 in order to measure the number and size of particles within the transparent tube 1. The diffraction scanning device 9 is preferably a laser diffraction scanner.

Figure 4:
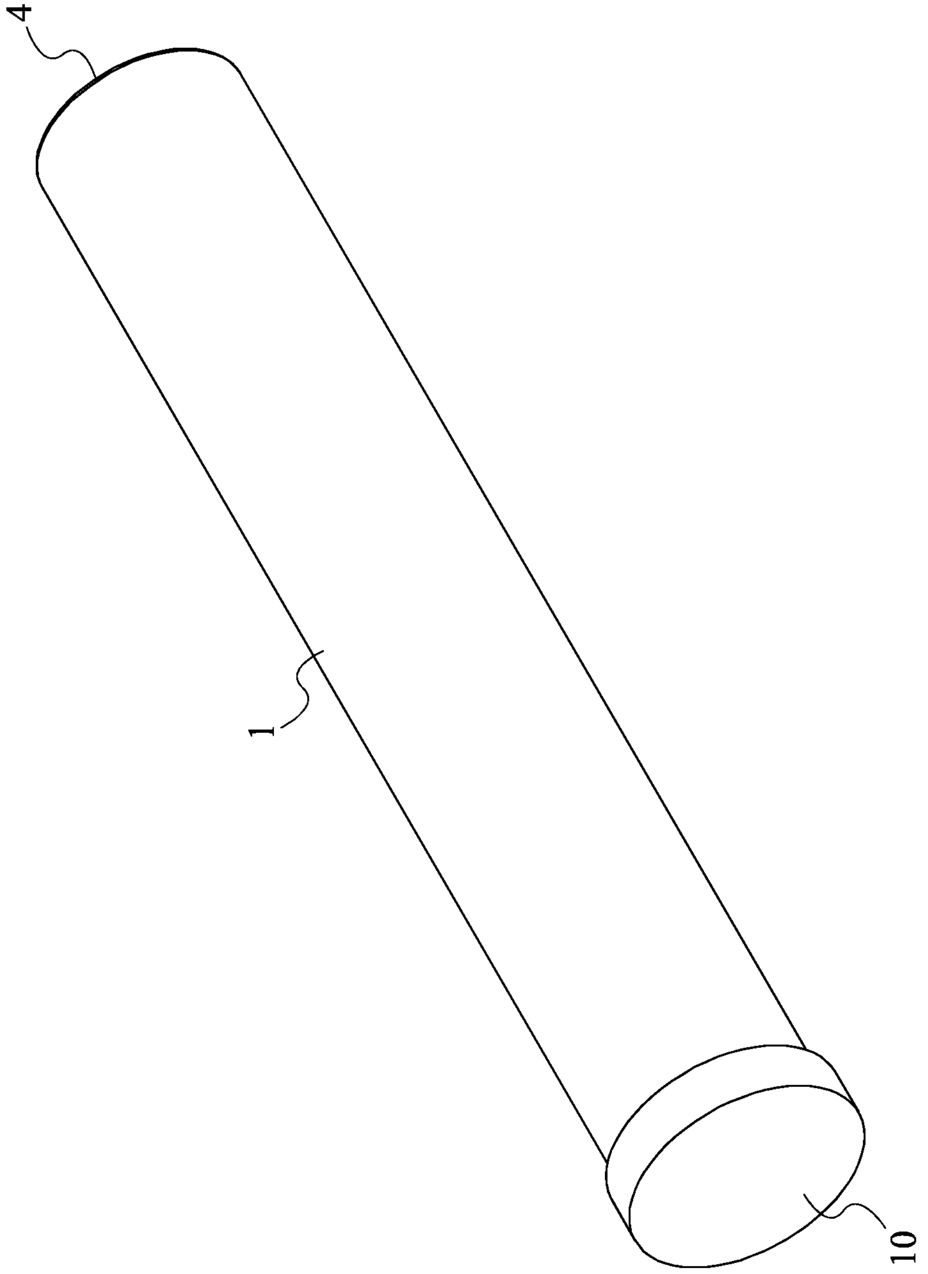
FIG. 4 is a perspective view of the present invention in a closed state.
Figure 5:
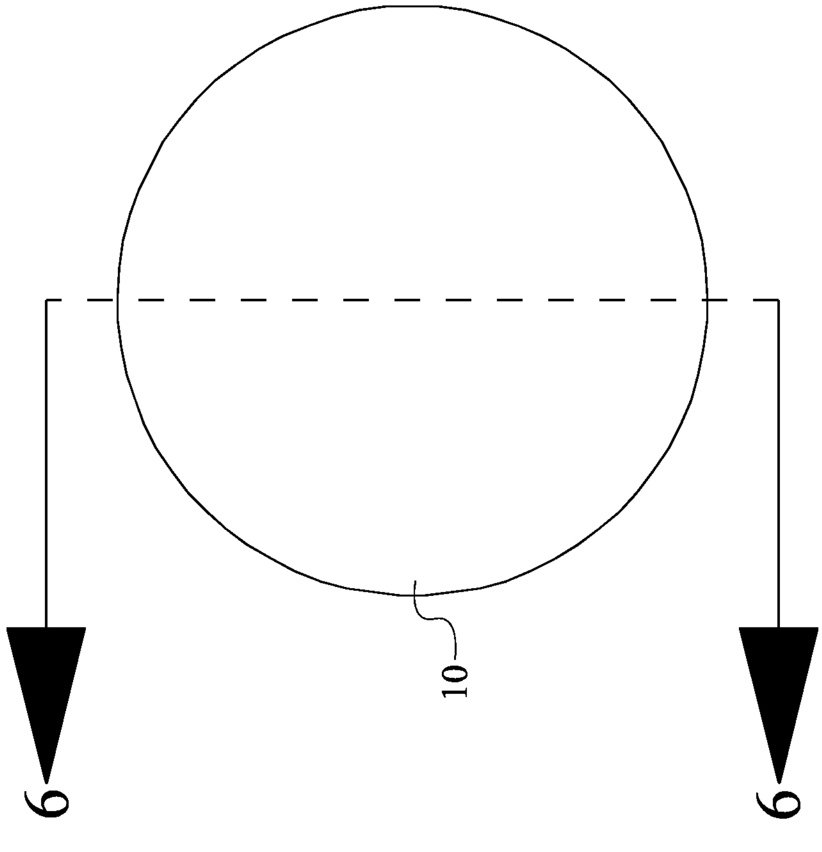
FIG. 5 is a front view of the present invention in the closed state.

In order to create the closed system of the present invention and with reference to FIGS. 4 and 6, the present invention may further comprise a cap 10. The cap 10 is hermetically attached to the first open end 2. This arrangement provides an airtight connection between the cap 10 and the transparent tube 1 in order to close off the first open end 2. The cap 10 is hermetically attached to the first open end 2 after the individual releases exhaled air into the transparent tube 1 so that the exhaled air trapped within the transparent tube 1 for future analysis by the diffraction scanning device 9.

As mentioned previously, the quantity of first antibodies 7 may be suspended within the transparent tube 1 through various methods. Preferably and with reference to FIG. 3, the present invention may further comprise a first mesh 11 as one of those methods. The quantity of first antibodies 7 is suspended within the transparent tube 1 by the first mesh 11. In further detail, the first mesh 11 is attached to an inner lateral surface of the transparent tube 1, and the quantity of first antibodies 7 is retained by the first mesh 11.

In order for the deformable dispenser 4 to effectively allow an individual to drive the quantity of second antibodies 8 to mix the complex formed by the exhaled air and the quantity of first antibodies 7 and with reference to FIGS. 3 and 6, the deformable dispenser 4 comprises a release portion 5 and a press portion 6. The release portion 5 is the portion of the deformable dispenser 4 in communication with the inner area of the transparent tube 1. The press portion 6 is the portion of the deformable dispenser 4 external to the inner area of the transparent tube 1. The release portion 5 and the press portion 6 are positioned opposite to each other about the deformable dispenser 4. Thus, the individual does not contact the contents within the transparent tube 1 when pushing the press portion 6 towards the transparent tube 1, which drives the quantity of second antibodies 8 to mix the complex formed by the exhaled air and the quantity of first antibodies 7. Further, the release portion 5 is positioned coincident with the second open end 3. This arrangement ensures the quantity of second antibodies 8 is as far as possible from the quantity of first antibodies 7 in order to prevent a premature mixture between the quantity of first antibodies 7 and the quantity of second antibodies 8.

As mentioned previously, the quantity of second antibodies 8 may be suspended within the deformable dispenser 4 through various methods. Preferably and with reference to FIG. 3, the release portion 5 is preferably a second mesh as one of those methods. The second mesh is positioned across the second open end 3. This arrangement positions the second mesh to retain the quantity of second antibodies 8 as far as possible from the quantity of first antibodies 7.

In order to easily acquire the quantity of first antibodies 7, the quantity of first antibodies 7 is a type of monoclonal antibodies. Thus, the quantity of first antibodies 7 is a set of antibodies that are generated in a laboratory setting to specifically interact with the target matter. Similarly, the quantity of second antibodies 8 is also a type of monoclonal antibodies. Thus, the quantity of second antibodies 8 is a set of antibodies generated in a laboratory setting to specifically interact with the complex formed by the quantity of first antibodies 7 and the target matter present in the exhaled air. Hence, both the quantity of first antibodies 7 and the quantity of second antibodies 8 are specifically developed for the viral or other target matter. Being monoclonal, these two antibodies are each of a specific size that is known and thus, identifiable in their free and combined form using diffraction technology. Both the quantity of first antibodies 7 and the quantity of second antibodies 8 are a type of monoclonal antibodies that allow the present invention to accurately detect specific viral particles or other particular matter.

In order to facilitate the mixing of the exhaled air with the quantity of first antibodies 7 and then the mixing of the resulting complex with the quantity of second antibodies 8 and with reference to FIG. 6, the present invention may further comprise a quantity of nebulized solvent 12. The quantity of nebulized solvent 12 is positioned within and throughout the transparent tube 1. In further detail, a nebulizer may be used to form and inject the quantity of nebulized solvent 12 into the transparent tube 1. The quantity of nebulized solvent 12 may be any type of solvent, but the nebulized solvent is preferably water.

Although the invention has been explained in relation to its preferred embodiment, it is to be understood that many other possible modifications and variations can be made without departing from the spirit and scope of the invention as hereinafter claimed.

What is claimed is:

1. A closed system for enlarging viral and bacterial particles for identification by diffraction scanning comprises:
- a transparent tube;
- a deformable dispenser;
- a quantity of first antibodies;
- a quantity of second antibodies;
- a diffraction scanning device;
- a quantity of nebulized solvent;
- the transparent tube comprises a first open end and a second open end;
- the deformable dispenser being hermetically connected to the second open end;
- the quantity of first antibodies being suspended within the transparent tube, adjacent to the first open end;
- the quantity of second antibodies being suspended within the deformable dispenser;
- the diffraction scanning device being positioned offset from the transparent tube;
- the diffraction scanning device being in optical communication with the transparent tuber; and
- the quantity of nebulized solvent being positioned within and throughout the transparent tube.

2. The closed system for enlarging viral and bacterial particles for identification by diffraction scanning as claimed in claim 1 further comprises:
- a cap; and
- wherein the cap being hermetically attached to the first open end.

3. The closed system for enlarging viral and bacterial particles for identification by diffraction scanning claimed in claim 1 further comprises:

a first mesh; and wherein the quantity of first antibodies being suspended within the transparent tube by the first mesh.

4. The closed system for enlarging viral and bacterial particles for identification by diffraction scanning as claimed in claim 1 wherein:

the deformable dispenser comprises a release portion and a press portion;

the release portion and the press portion being positioned opposite to each other about the deformable dispenser; and the release portion being positioned coincident with the second open end.

5. The closed system for enlarging viral and bacterial particles for identification by diffraction scanning as claimed in claim 4 wherein:

the release portion being a second mesh; and the second mesh being positioned across the second open end.

6. The closed system for enlarging viral and bacterial particles for identification by diffraction scanning as claimed in claim 1, wherein the quantity of first antibodies is a quantity of first monoclonal antibodies.

7. The closed system for enlarging viral and bacterial particles for identification by diffraction scanning as claimed in claim 1, wherein the quantity of second antibodies is a quantity of second monoclonal antibodies.

8. The closed system for enlarging viral and bacterial particles for identification by diffraction scanning as claimed in claim 1, wherein the diffraction scanning device is a laser diffraction scanner.

9. The closed system for enlarging viral and bacterial particles for identification by diffraction scanning as claimed in claim 1, wherein the quantity of nebulized solvent is water.

10. A closed system for enlarging viral and bacterial particles for identification by diffraction scanning comprises:

a transparent tube;

a deformable dispenser;

a quantity of first antibodies;

a quantity of second antibodies;

a diffraction scanning device;

a first mesh;

a quantity of nebulized solvent;

the deformable dispenser comprises a release portion and a press portion;

the release portion and the press portion being positioned opposite to each other about the deformable dispenser;

the transparent tube comprises a first open end and a second open end;

the deformable dispenser being hermetically connected to the second open end;

the quantity of first antibodies being suspended within the transparent tube, adjacent to the first open end;

the quantity of second antibodies being suspended within the deformable dispenser;

the diffraction scanning device being positioned offset from the transparent tube;

the diffraction scanning device being in optical communication with the transparent tube;

the quantity of first antibodies being suspended within the transparent tube by the first mesh;

the release portion being positioned coincident with the second open end;

the quantity of nebulized solvent being positioned within and throughout the transparent tube.

11. The closed system for enlarging viral and bacterial particles for identification by diffraction scanning as claimed in claim 10 further comprises:

a cap; and wherein the cap being hermetically attached to the first open end.

12. The closed system for enlarging viral and bacterial particles for identification by diffraction scanning as claimed in claim 10 wherein:

the release portion being a second mesh; and the second mesh being positioned across the second open end.

13. The closed system for enlarging viral and bacterial particles for identification by diffraction scanning as claimed in claim 10, wherein the quantity of first antibodies is a quantity of first monoclonal antibodies.

14. The closed system for enlarging viral and bacterial particles for identification by diffraction scanning as claimed in claim 10, wherein the quantity of second antibodies is a quantity of second monoclonal antibodies.

15. The closed system for enlarging viral and bacterial particles for identification by diffraction scanning as claimed in claim 10, wherein the diffraction scanning device is a laser diffraction scanner.

16. The closed system for enlarging viral and bacterial particles for identification by diffraction scanning as claimed in claim 10, wherein the quantity of nebulized solvent is water.

* * * * *